United States Patent [19]

Welch

[11] 4,047,102
[45] Sept. 6, 1977

[54] DUAL CHAMBER, HIGH SENSITIVITY GAS SENSOR AND PUMP

[75] Inventor: Kimo M. Welch, Mountain View, Calif.

[73] Assignee: Varian Associates, Palo Alto, Calif.

[21] Appl. No.: 682,554

[22] Filed: May 3, 1976

Related U.S. Application Data

[63] Continuation of Ser. No. 519,369, Oct. 30, 1974, abandoned.

[51] Int. Cl.$^2$ ............................................. G01N 27/00
[52] U.S. Cl. .................................... 324/33; 23/254 F
[58] Field of Search ............ 324/33; 73/4 V, 388 BN; 417/49, 51; 23/254 F

[56] References Cited

U.S. PATENT DOCUMENTS

| 3,355,587 | 11/1967 | Jenckel ................................. 73/40.7 |
| 3,683,272 | 8/1972 | Vissers et al. ........................ 324/33 |

OTHER PUBLICATIONS

Freakes et al., "The Performance Characteristics of Three Types of Extreme High-Vacuum Gauges", Trans 10th A.V.S. Nat. Vac. Symp. 1963 pp. 257-262.

Moraw, G. "The Influence of Ionization Gauges on Gas Flow Measurement Vacuum", vol. 24 3-1974 pp. 125-128.

Loehrig et al. "Accurate Calibration of Vacuum Gauge to 10$^{-9}$ to RR," Trans. 8th A.V.S. Nat. Vac. Symp. 1961 pp. 511-518.

Primary Examiner—Rudolph V. Rolinec
Assistant Examiner—Vincent J. Sunderdick
Attorney, Agent, or Firm—Stanley Z. Cole; Leon F. Herbert; Edward J. Radlo

[57] ABSTRACT

Apparatus for measuring gas comprising a gas sensing unit having a gas inlet membrane and being evacuated by a sputter ion pump via a restrictive conductance. Said conductance has a very low value relative to the pumping speed of the pump, whereby a change in the pumping speed of the pump causes substantially no change in the pumping speed with which the gas sensing unit is evacuated, so that the output signal of said gas sensing unit is a true reflection of the gas entering said inlet, without distortion which would otherwise be caused by changes in pumping speed of said pump.

19 Claims, 3 Drawing Figures

DUAL CHAMBER, HIGH SENSITIVITY GAS SENSOR AND PUMP This is a continuation division of application Ser. No. 519,369, filed Oct. 30, 1974, now abandoned.

BACKGROUND OF THE INVENTION

A. Field of the Invention

This invention relates to an apparatus and method for measuring the concentration of gas present at the inlet membrane of the apparatus and more particularly to a dualchamber sensor and pump for accurately measuring the concentration of gas by means of ionizing the gas.

B. Description of Prior Art

It is known to measure the concentration of a gas by means of using an ion pump to create a vacuum in a chamber, ionizing the gas and measuring the current within the ion pump produced by the ionization of the gas as a reflection of the concentration of the gas. This method normally utilizes a thin metal membrane or diaphram (interface) immersed in a solution (either a liquid or gas mixture) which permits the passage of gas through the membrane and into the vacuum chamber. The gas ionized in the pump is attracted to a cathode which is made of gettering material, is sorped thereunto, and is converted into an electrical current. This method is described, for example, in U.S. Pat. No. 3,683,272, issued Aug. 8, 1972 to Vissers et al. entitled "Method and Apparatus for Determining Hydrogen Concentration in Liquid Sodium Utilizing Ion Pump to Ionize the Hydrogen". This technique, however, has several well-known disadvantages, which are discussed, for example, in Vissers et al., "Hydrogen-Meter Leak Detector for LMFBR Steam Generators", published by Argonne National Laboratory in October, 1973. See also Turner, et al. "Penning Discharge Getter-Ion Pumps", I.E.E.E. Trans. on Nuclear Science, Volume NS-14, No. 3 (June 1967). These disadvantages relate to the fact that the pumping speed of the ion pump changes during the course of the measurement and this in turn affects the results of the measurement itself. A case where the equipment influences the subject of the test is a highly undesirable situation. More specifically, in the case of pumping hydrogen, unwanted hydrides tend to form on the cathode. The rate at which these hydrides form and hydrogen is sorbed and goes into solution with the cathode material is dependent on the surface condition of the cathode material. Chemical compounds formed by other gases and the cathode material and other forms of contamination may drastically alter the ability of the cathode to pump hydrogen. Pumping sites, that is, locations on the cathode where reactions take place, change. Attempts have been made to precondition the cathodes by argon sputtering to stabilize the cathodes but these approaches have met with only limited success. Another problem is that the diffusion rates in the bulk metal of the cathodes are variable. Consequently the pumping speed within the pump is a function of the history of the pump, the time it has been used, and how it has been used. All of this means that the ion pump current changes with time, and may in turn indicate a change in pumping speed of the pump, masking changes in the concentration of the gas at the instrument interface.

Also, with the exception of unwanted ion current changes stemming from changes in pump speed, the sensitivity of known instruments is fixed. If one changes the size of the pump by either increasing or decreasing the number of discharged cells or elements, the total ion current will be invariant for the same concentration of gas in solution or chemical reaction rate at the instrument interface. What is needed is a more sensitive and accurate device to measure the concentration of the gas at the gas-instrument interface in which the result is independent of the equipment being used.

OBJECTS OF THE INVENTION

It is a primary object of the present invention to provide an improved apparatus and method to measure the concentration of gas at the instrument interface where the related signal is, to a very close approximation, independent of the equipment being used.

It is a further object of the invention to provide a gas sensor which to a very close approximation is independent of the pumping speed of the vacuum pump being utilized.

It is another object of the invention to provide a gas sensor with a longer life than is available in the prior art.

It is a still further object of the present invention to provide a gas sensor which is more accurate than that of the prior art.

It is another object of the present invention to provide a gas sensor which serves as a current amplifier.

It is a still further object of the present invention to provide a gas sensor which is more sensitive and which features better long term and short term stability than that available in the prior art.

It is another object of the present invention to provide a sensor which can be used in both static and dynamic mode.

It is a still further object of the instant invention to provide a detector for water leaking into liquid sodium and which can be utilized as a gas concentration monitor.

It is another object of the instant invention to provide a hydrogen sensor which can be utilized as both a water leak detector and a hydrogen concentration monitor.

It is a still further object of the instant invention to provide a hydrogen sensor having two chambers wherein one chamber performs a pumping function and another chamber performs a sensing function It is a still further object of the present invention to provide a gas sensor having a plurality of chambers wherein one chamber performs a pumping function and all but one chamber performs sensing functions.

It is another object of the instant invention wherein it may be used as a hydrogen flux monitor wherein ion current measured may be used to indicate chemical reaction rates which may occur at the instrument interface.

It is another object of the present invention to measure the pressure of a gas in a chamber with a high degree of accuracy.

It is a still further object of the instant invention to ascertain the pumping speed of a sputter-ion pump and to make the speed invariant.

It is a further object of the instant invention to power a gas sensor having a plurality of chambers with a single power supply.

SUMMARY OF THE INVENTION

Briefly and in accordance with the above objects, the present invention is concerned with an apparatus and method for measuring the concentration of gas in a solution utilizing a multi-chambered gas pump configuration. In the preferred embodiment two chambers are used, each of which is in the form of a Penning discharge device. Any gas pump may be used for the pumping chamber, however, such as a diffusion pump, a cryogenic pump, other electronic gettering pumps, and forms of mechanical vacuum pumps. Each chamber comprises an anode and a cathode, although other configurations may be used without departing from the spirit of the instant invention, such as the addition of a grid or grids. The gas is made to permeate through a thin metal membrane or porous membrane into the first chamber. The first chamber senses the gas by ionizing the gas and converting the ions into electrical current.

The pumping caused by the first chamber is negligible because the cathode of this chamber consists of passive elements precluding any appreciable pumping effect. In other words, no gas particles leave the first chamber via its cathode; the gas ions are merely neutralized on the cathode. A small aperture or restrictive conductance connects the first chamber with the second chamber. The purpose of the second chamber is to remove the gas from the system, create and sustain a vacuum, and to pump in the traditional sense of the prior art (as well as gas ions being neutralized on the cathode, gas particles combine with it by chemical and physical means). In this second chamber the cathode is of the chemically active type. Therefore, there is pumping with inherent speed changes. But, since the activity in the first chamber is essentially independent of that in the second chamber, the measurement of the gas pressure in the first chamber is not significantly affected by the change of pumping speed in the second chamber.

The instant invention may be used in either a dynamic or static mode. When used in dynamic mode, the invention has features of stability, accuracy and sensitivity far superior to known instruments.

Each chamber may comprise a plurality of cells, in which case each cell comprises a cathode/anode combination.

In a further embodiment, a single pumping chamber may be used to support a plurality of sensing chambers, each of which may be monitoring a different gas. The pumping speed with which each sensing chamber is evacuated is virtually independent of the pumping speed of the pumping chamber.

BRIEF DESCRIPTION OF THE DRAWING

These and other more detailed and specific objects and features of the instant invention are disclosed in the following specification, reference being has to the accompanying drawing in which.

DETAILED DESCRIPTION OF THE DRAWING

Figure 1:
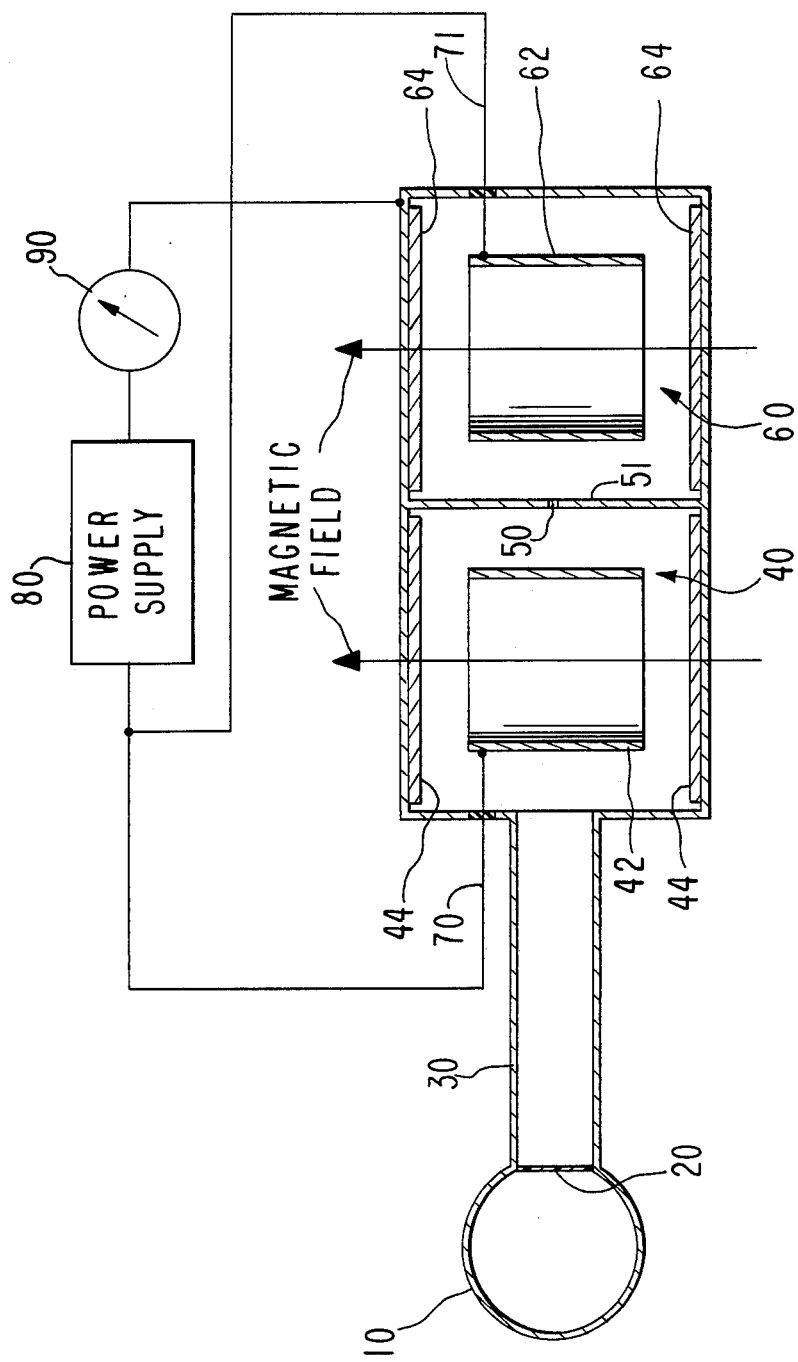
FIG. 1 is a cross-sectional representation of one embodiment of the instant invention.

As an example of one embodiment of the instant invention, it is used to measure gas, which may be dissolved in solution, present in chamber 10. The gas is permitted to pass through a membrane 20 which allows transmission of the gas of interest but no transmission of the remaining solvent or gasses. The gas of interest passes through a connecting conduit 30 into sensing chamber 40 and through a restrictive conductance 50 (e.g., a narrow hollow tube or aperture) into pumping chamber 60 where it is pumped. Preferably, conductance 50 is formed as a small aperture in the otherwise solid wall 51 which separates chambers 40 and 60. Sensing chamber 40 and pumping chamber 60 are each Penning discharge devices which ionize the gas and produce an electrical current flow through cathodes 44 and 64 in the respective chambers. The sensing activity is performed by sensing chamber 40 which contains anode 42, and a cathode 44 which is fabricated of a nonactive material such as stainless steel. Gas ions are neutralized on cathode 44 but gas particles are not sorbed (pumped) on cathode 44 or other surfaces in the chamber. The pumping activity is performed by pumping chamber 60 which contains anode 62 and an active gettering material such as titanium or tantalum as cathode 64 for sorption of the ionized gas. the anodes 42 and 62 are hollow cylindrical metal members each forming a single anode cell. The anodes are connected to one terminal of power suppy 80 via leads 70 and 71 which are electrically insulated as they pass through the walls of chambers 40 and 60, respectively. Current measuring means 90 are situated on the electrical connection line between the other terminal of power supply 80 and cathodes 44 and 64. Gas ions are neutralized on cathode 64 and gas particles leave the system via the active sorption action of cathode 64. A greater current, however, is drawn through cathode 44 as will be illustrated below. Sensing chamber 40 and pumping chamber 60 can each contain more than one anode as disclosed in U.S. Pat. No. 2,993,638, or more than one cell each of which comprises an anode and a cathode corresponding to anode/cathode combination 42/44 or 62/64. A magnetic circuit (not shown) provides a magnetic field permeating sensing chamber 40 and pumping chamber 60 parallel to the axis of the anode cells and serves to extend, spatially and temporally, the paths of electrons within sensing chamber 40 and pumping chamber 60, thus enabling the electrons to ionize a greater number of gas molecules.

DETAILED DESCRIPTION OF THE PREFERRED EMBODIMENT

A gas is present in chamber 10; it may be dissolved in solution. The gas may be any gas although the typical and perhaps most important application of this invention is when the gas to be detected is hydrogen, $H_2$.

For example, in a sodium leak detector application, a palladium diaphram 20 is used in a system to measure $H_2$ which is liberated when liquid soidum used to carry heat from a nuclear reactor leaks out of its containment pipe into an atmosphere containing a hydrogen-liberating substance.

In another highly important application, the invention is used to measure hydrogen dissolved in the liquid sodium. In this use of the invention, chamber 10 is the pipe containing the liquid sodium used to draw off heat from the reactor. The sodium pipe goes through a succession of heat exchangers to further reduce the heat. In one of the exchangers the heat is transferred from a sodium coolant system to a water coolant system. If there were a leak of water into the sodium line in this portion of the system, a reaction would take place causing rapid corrosion and erosion of the metal tubes adjacent to the leak. A sufficiently large or long lasting leak could result in the deformation and rupture of the reactor itself. Hence, it is imperative that even the smallest water leaks into the sodium line be detected immediately if propagation of damage is to be avoided. One of the byproducts of such a leak would be the production of hydrogen dissolved in the molten or liquid sodium. Hence, in this use the instant invention may be termed a water leak detector. In such an application membrane 20 is a thin nickel diaphragm which is transparent to hydrogen and can withstand the corrosive effects of the molten sodium. The water leak detector is operated in what is referred to as the dynamic equilibrium mode in order to provide early warning of a leak condition. Ion pump current is used as the indicator of hydrogen flux through the nickel diaphragm. This current is continuously monitored and any appreciable increase signals a leak warning. In prior art systems the variations in pumping speed inherent in all ion pumps caused by complicated processes of chemisorption and physisorption of hydrogen result in large variations of current in the closed system from which one might erroneously conclude that the concentration of hydrogen in the molten sodium has changed. In the present invention, however, the sensing means, sensing chamber 40, is isolated from the pumping means, pumping chamber 60, and the variation in pumping speed in chamber 60 does not affect the sensing of the hydrogen which transpires in chamber 40.

In prior art installation it was customary to connect a vacuum gauge to the measuring system between the interface 20 and the sputter ion pump, and provide a valve between the gauge connection and the sputter ion pump. One type of vacuum gauge used for this purpose is the gauge sold by Varian Associates under the trademark "Millitorr". Periodically the valve was closed and the equilibrium pressure read from the gauge was used as a gas concentration monitor, particularly for hydrogen gas. The gauge reading was used periodically to provide continuing calibration of the sputter ion pump current to correct for changes in pumping speed. However, since the current reading from the present invention is substantially independent of pumping speed, the present instrument does not require continuing calibration checks. On the other hand, design of the instant instrument still facilitates incorporation of the valve and vacuum gauge of a known hydrogen concentration monitor should the option of this added feature prove desirable.

The invention may also be used as a chemical reaction rate monitor in the case where the instrument interface is in or forms part of a chamber in which the chemical reaction is taking place.

The stability and consistancy of the instant invention in pumping hydrogen will now be described.

Let S be the pumping speed of the sputter ion pump formed in chamber 60. The speed, normally measured in liters/second, is (within the range of normal operating conditions) independent of the pressure of the gas in the system and the quantity of gas moving in (flux). The pumping speed is dependent upon the geometry of the pump, electrical potential on anode 62 and cathod 64, magnetic field, and the chemical acitivity of the pump. Let C be the conductance of restrictive conductance 50. C is normally measured in liters/second and is given by the following equation:

$$C = A\sqrt{kT/2\pi m}$$

where $A$ is the area of the conductance in centimeters squared, $k$ is the Boltzmann constant, $1.38 \times 10^{-16}$ erg/deg, $T$ is the absolute temperature of the gas being measured (in this regard it is important to note that this temperature in actual operation is normally the temperature of the chamber, not the temperature of the gas in the molten solvent, since the gas moving into the chamber quickly assumes the temperature of the chamber), and $m$ is the molecular weight of the gas being measured. Page 19 of A. Guthrie and R. K. Wakerling, *Vacuum Equipment and Techniques*, McGraw Hill (1949).

It is known in the art that the effective pumping speed of a pump in series with a known vacuum conductance is given by the formula:

$$(1/s_{eff}) = (1/C) + (1/S_P)$$

where $S_{eff}$ is the effective pumping speed of the conductance/pump combination, and $S_P$ is the pumping speed of the pump. Guthrie and Wakerling, supra, page 15. With respect to the accompanying drawing this is:

$$(1/S_{40}) = (1/C_{50}) + (1/S_{60})$$

where $S_{40}$ is the pumping speed with which sensing chamber 40 is evacuated, $C_{50}$ is the conductance of conductance 50, and $S_{60}$ is the pumping speed of the pumping chamber 60.

Solving for $S_{40}$, we obtain $$S_{40} = C_{50}S_{60}/(C_{50} + S_{60})$$

If $C_{50}$ is very much smaller than $S_{60}$, then we see that:

$$S_{40} \approx C_{50}$$

In other words, $S_{40}$ is substantially independent of $S_{60}$. Thus $S_{60}$ may be allowed to change as a result of chemical activity on cathode 64 but $S_{40}$ will remain essentially a constant, permitting precise measurements within sensing chamber 40. As a specific example, let us assume that $C_{50} = 0.1$ liter/second, that $S_{60}$ at time $t_1$ is 5 liters/second and that $S_{60}$ at time $t_2$ is 2.5 liters/second. In other words, the pumping speed in pumping chamber 60 varies by a factor of 2 between times $t_1$ and $t_2$. The variation in pumping speed with which sensing chamber 10 is evacuated is given as a ratio of its pumping speed at the two times as follows;

$$\frac{S_{40}(t_1)}{S_{40}(t_2)} = \frac{\frac{S_{60}(t_1) C_{50}}{S_{60}(t_1) + C_{50}}}{\frac{S_{60}(t_2) C_{50}}{S_{60}(t_2) + C_{50}}} = \frac{S_{60}(t_1) C_{50} (S_{60}(t_2) + C_{50})}{S_{60}(t_2) C_{50} (S_{60}(t_1) + C_{50})} \approx 1.029$$

Thus we see that the pumping speed with which sensing chamber 40 is evacuated has hardly changed at all.

Now Q, the flux of the gas permeating through membrane 20, is normally measured in Torr liters/second and is given by the following formula:

$$Q = SP$$

where $S$ is the pumping speed in liters per second at which chamber 40 is being evacuated and $P$ is the pressure in chamber 40, normally measured in Torr.

If the pumping speed with which sensing chamber 40 is evacuated is constant, it follows from the above equation that the pressure change in the chamber depends solely upon the change in Q or flux. Now the current I passing through cathode 44 is directly proportional to the pressure P for a given geometry of the chamber and electrical and magnetic field parameters. This linearity can be maintained over a wide range of values by selecting appropriate values for the geometry and construction parameters of the chamber, for example, the size of aperture 50, the size, thickness and material of membrane 20, and the geometric values of sensing chamber 40. In other words, a simple electrical measurement of the current I through cathode 44 will give us a measurement of P and in turn a measurement of Q (since S is known from the reltionship $S_{40} \simeq C_{50}$). This in turn gives us a measurement of the concentration of hydrogen or other gas of interest in chamber 10, because the value of the concentration of gas depends only upon Q and the temperature of membrane 20.

An important advantage of the instant invention is that the device can be used as a gas concentration monitor. This is because, as indicated above, the pumping speed with which the sensing chamber is evacuated is approximately equal to $C_{50}$ and is constant. Since we can calculate $C_{50}$ from a group of physical constants, we can determine $S_{eff}$ (the effective pumping speed with which chamber 40 is being evacuated), and from the equation $$Q = S_{eff} P$$

determine the absolute concentration of hydrogen or other gas in the system. In prior art systems in which the pump and measuring unit were combined in the form of a single sputter ion pump, the pumping speed was neither measurable nor invariant.

An important feature of the instant invention is that it functions as a current amplifier. In other words for a given Q the present invention will develop a higher current than the prior art. This will be demonstrated after first showing that changing the ion pump size in known instruments does not affect sensitivity.

Assume that a unit pumping element (single anode/cathode cell) has a speed of $S_u$. Two such elements used in concert will have a speed $2S_u$, and $n$ unit elements $nS_u$ speed. By the same token for the same geometry and electrical and magnetic field parameters, the current drawn by each element will be, to a close approximation, directly proportional to pressure. That is to say for the unit element, $I = k_u P$ (where P is the pressure in a unit element and $k_u$ is the proportionally constant for the unit element) whereas for two unit elements, $I = 2k_u P_2$ and for $n$ unit elements $I_n = nk_u P_n$ where $P_n$ is the pressure in each unit element when there are $n$ unit elements.

It will now be demonstrated that for the same Q, the current drawn by a pump with a unit pumping elements will be the same as the current drawn by a pump with $m$ unit pumping elements. Note that $P_m \neq P_n$, because as you increase the number of pumping elements you decrease the pressure.

$$\sum_{i=1}^{m} S_i P_m = Q = \sum_{i=1}^{n} S_i P_n; \; P_n = \frac{\sum_{i=1}^{m} S_i P_m}{\sum_{i=1}^{n} S_i}$$

$$\therefore \frac{I_n}{I_m} = \frac{k_n P_n}{k_m P_m} = \frac{nk_u P_n}{mk_u P_m} = \frac{nP_n}{mP_m} = \frac{n}{mP_m} \cdot \frac{\sum_{i=1}^{m} S_i P_m}{\sum_{i=1}^{n} S_i}$$

$$= \frac{n}{mP_m} \cdot \frac{mS_u P_m}{nS_u} = 1$$

On the other hand, compare the current drawn by a known instrument with $n$ pumping elements to that of the instant invention with a sensing chamber and a pumping chamber. For a given Q and $n$ pumping elements, the total current drawn will be $$I_n = nk_u(P_n) = nk_u(Q/nS_u) = k_u Q/S_u. \text{ (known instrument)}$$

For the instant invention there will be two current components. Assume the pumping chamber has the same parameters as given for the known instrument. Then for the same Q one current component will also be $(k_u Q/S_u)$, but there is also a current component drawn by the sensing chamber albeit no pumping. Assume that this sensing chamber has $m$ unit elements. Then, as we know from the prior art (Guthrie and Wakerling, supra, page 35) and where subscripts $m$ and $n$ relate to chambers 40 and 60 respectively $$Q = C(P_m - P_n)$$

$$P_m = \frac{Q}{C} + P_n.$$

Then $I_m = k_m(P_m) = mk_u(P_m)$ or $I_m = mk_u \left( \frac{Q}{C} + P_n \right)$ $$= mk_u \frac{Q}{C} + \frac{Q}{nS_u}.$$

Figure 2:
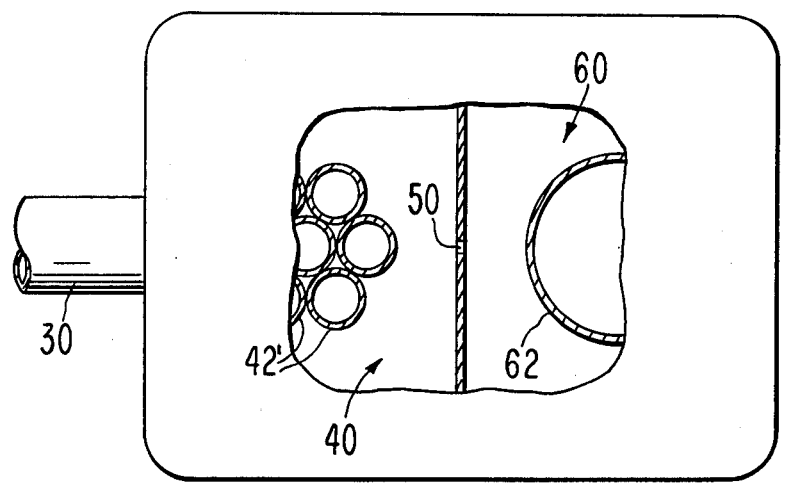
FIG. 2 is a top view partly in section showing another embodiment employing plural cells in the sensing unit.

In other words for a given Q, the current in the sensing chamber increases in direct proportion to the number of unit cells added to that chamber. This is because the sensing cells perform substantially no pumping and therefore adding cells in chamber 40 does not reduce pressure in that chamber. Such a multiple sensing cell arrangement is shown in FIG. 2 in which 42' indicates the multiple cells in chamber 40. The current amplication (ratio of the total current drawn by the instant invention compared with that of the known instrument) is:

$$\frac{I_{total} \text{ (instant)}}{I_{total} \text{ (known)}} = \frac{I_m + I_n}{I_n} =$$

$$\frac{mk_u \left( \frac{Q}{C} + \frac{Q}{nS_u} \right) + \frac{k_u Q}{S_u}}{\frac{k_u Q}{S_u}}$$

or current amplification = $(mS_u/C + 1)$. Assume the least advantageous configuration of $m=1 >> n$. Inasmuch that $S_u >> C, (S_u/C + 1 + (1/n) >> 1.$ Typically $10 \leq (S_u/C \leq 100$. Assume $S_u/C = 20$. Then the amplication will be $\approx 21$. Because of the current amplication feature of the instant invention it is possible to use the same high voltage power supply to operate each of the separate chamber 40 and 60, thus resulting in a savings of instrumentation costs. Even though large variations in pump speed may occur this is possible. For example, assume that the speed of the pumping chamber is decreased by a factor of two. The ratio of the total current drawn in the two cases, for the least advantageous configuration, would be 22/21 or a change of 4.8%. Note that most of the current is drawn through the sensing chamber because the pressure in it is higher than in the pumping chamber. The ratio of current drawn through the sensing chamber to that drawn through the pumping chamber is given by $$\frac{I_m}{I_n} = \frac{mk_u\frac{Q}{C} + \frac{m}{n} k_u \frac{Q}{S_u}}{k_u \frac{Q}{S_u}} = \frac{mS_u}{C} + \frac{m}{n} = m\left(\frac{S_u}{C} + \frac{1}{n}\right)$$

Since one of our assumptions is that $S_u >> C$, it follows that $I_m >> I_n$. Thereforem most of the current amplication is obtainable from reading just $I_m$. However, a simplified power supply configuration may be used in which $I_m + I_n$ is measured, and very little error deviation from the true $I_m$ value is introduced.

The isolation of the sensing functions and pumping functions, and the consequent current amplification feature, permits a much greater sensitivity in the device. Because of this sensitivity, it is possible to decrease the size of membrane 20 by at least an order of magnitude and still retain the same accuracy of measurement. Since Q is directly proportional to the area of membrane 20, Q also decreases by an order of magnitude. A high measurement accuracy coupled with a low Q means that the life of the pump increases dramatically because a fewer number of molecules entering through membrane 20 means that cathode 64 is not subject to as much ion bombardment and thus lasts longer. This is an important advantage of the instant invention.

The material used for cathode 64 is typically titanium or an alloy of same although any active gettering material for sorption of the ionized particles will do. The material utilized for cathode 44 is typically stainless steel, although any non-active cathode material that is a passive element precluding a pumping effect will do.

The increased sensitivity of the device results also in an increased accuracy at lower signal levels; this is another important advantage of the instant invention.

Figure 3:
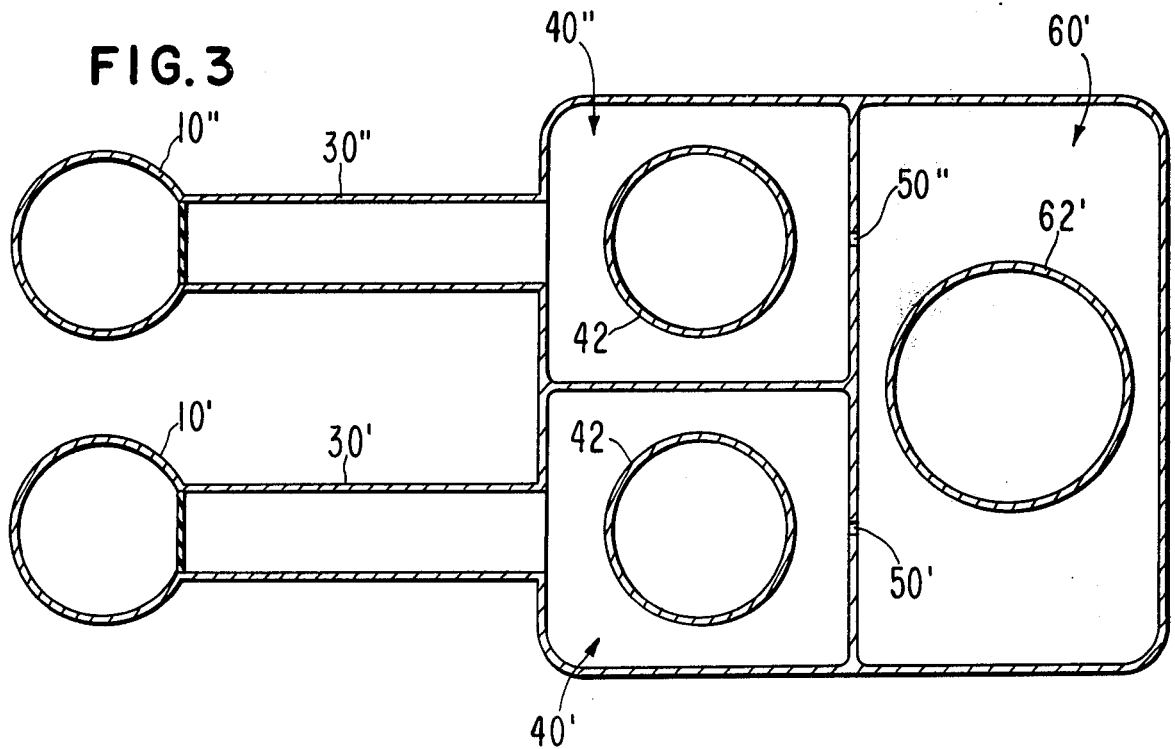
FIG. 3 is a cross-sectional view of a further embodiment showing plural sensing units connected to a single pumping unit.

The concepts of the invention may be extended by placing a number of sensors similar to sensing chamber 40 in parallel, all connected to and pumped by a single large ion pump corresponding to pumping chamber 60. The pumping speed of the pumping chamber must be very much larger than the conductance through which each sensing chamber is connected to the pumping chamber. In this case, each sensing chamber can be used to monitor a separate and distinct type or source of gas. Such a plural sensing chamber arrangement is shown in FIG. 3 in which prime and double prime numbers indicate parts corresponding to similar elements with unprimed numbers in FIG. 1.

While the principles of the invention have now been made clear in the illustrated embodiment shown above, there will be obvious to those skilled in the art many modifications in structural arrangement of components used in the practice of the invention without departing from the above enuniciated principles. For example, any type of vacuum gauge (e.g., Millitorr gauge) can be used for sensing chamber 40. The appended claims are therefore intended to cover and embrace any such modification within the limits only of the true spirit and scope of the invention.

What is claimed is:

1. Gas sensing apparatus comprising:
   a gas sensing unit; inlet means to said gas sensing unit comprising an inlet wall preferentially transmissive to gas under investigation;
   a gas pumping unit having means for pumping gas, and passage means forming a conductance interconnecting said sensing and pumping units;
   said sensing unit being constructed to have little or no pumping speed relative to the pumping speed of said pumping unit; and
   the value of said conductance being small relative to the pumping speed of said pumping unit, whereby in operation the pressure in said sensing unit is higher than the pressure in said pumping unit to provide high sensitivity.

2. Gas selective sensing apparatus comprising:
   means for selecting a gas from a plurality of unseparated gases for sensing said selected gas;
   an ion-forming and collecting unit having an anode, cathode means spaced from said anode, and means for forming a magnetic field for causing electrons to follow a circuitous route in reaching said anode, said ion-forming and collecting unit being connected to said gas selecting means;
   a sputter-ion pump unit having an anode, cathode means spaced from said anode, and means for forming a magnetic field for causing electrons to follow a circuitous route in reaching said anode, said cathode means in said sputter-ion pump unit being of a material which provides substantial pumping and said cathode means in said ion-forming and collecting unit being of a material which provides little or no pumping relative to the pumping provided by said sputter-ion pump unit;
   passage means forming a conductance interconnecting said pump unit and said ion-forming and collecting unit; and
   the value of said conductance being small relative to the pumping speed of said sputter-ion pumping unit, whereby in operation the pressure in said ion-forming and collecting unit is higher than the pressure in said pumping unit to provide high sensitivity.

3. Apparatus for sensing the content of particular gas in a container comprising:
   a sensing chamber whose interior cavity is coupled to said container via a membrane, said sensing chamber comprising at least one cell, said cell including an anode and a cathode, said membrane having gas specific transmission characteristics whereby in a mixture of gases a particular gas is selectively admitted to said sensing chamber, said cathode being chemically inert with respect to said selected gas; and
   a pumping chamber comprising a gas pump, said pumping chamber's interior cavity being coupled to the interior cavity of said sensing chamber via conducting means whose conductance is small in relation to the pumping speed of said pumping chamber, whereby in operation the pressure in said sensing chamber is higher than the pressure in said pumping chamber to provide high sensitivity.

4. Apparatus as in claim 3 wherein said membrane is fabricated of thin nickel.

5. Apparatus as in claim 4 wherein said sensing chamber cathode is fabricated of stainless steel.

6. Apparatus as in claim 3 wherein said pumping chamber comprises a sputter ion pump with at least one cell, said cell including an anode and a cathode, and said cathode being made of chemically active material.

7. Apparatus as in claim 6 wherein said pumping chamber cathode is fabricated of titanium.

8. Apparatus as in claim 6 further comprising a single power supply connected to both said sensing chamber cell and said pumping chamber cell, and means to measure the electrical current flowing through said single power supply.

9. Apparatus as in claim 6 wherein the number of cells in said sensing chamber is greater than the number of cells in said pumping chamber.

10. Apparatus as in claim 3 wherein said conducting means is an aperture in a wall between said sensing and pumping chambers.

11. Apparatus as in claim 3 further comprising means to measure the electrical current flowing through the cathode of said sensing chamber.

12. Apparatus as in claim 11 wherein said pumping chamber comprises a sputter ion pump having a cathode, and means to measure the current flowing through the cathode of said pumping chamber.

13. Apparatus as in claim 3 wherein a plurality of said sensing chambers are coupled to said pumping chamber, said coupling comprising conducting means linking each sensing chamber independently to said pumping chamber.

14. Apparatus for sensing gas present outside said apparatus comprising:
a sensing chamber having a gas-permeable inlet membrane, said sensing chamber comprising at least one sensor cell, said sensor cell comprising an anode and a chemically non-active cathode;
a pumping chamber comprising a sputter-ion pump with at least one pumping cell, said pumping cell comprising an anode and a chemically active cathode, the interior cavity of said pumping chamber being coupled to the interior cavity of said sensing chamber via a small aperture conducting means whose conductance is small in comparison with the pumping speed of said pumping chamber, whereby in operation the pressure in said sensing chamber is higher than the pressure in said pumping chamber to provide high sensitivity; and
means to measure the electrical current flowing through the cathode of said sensing chamber.

15. A method of sensing gas comprising the steps of:
communicating a pressure sensing unit with an unknown concentration of gas;
pumping gas out of said sensing unit by means of a pumping unit connected to the sensing unit via a restricted conductance;
said pumping being performed at a pumping speed which is high relative to the value of said conductance to obtain a pressure in said sensing unit which is higher than the pressure in said pumping unit to provide high sensitivity in said sensing unit; and
using the output of said pressure sensing unit to obtain information about said unknown concentration of gas.

16. The method of claim 15 wherein said pressure sensing unit has means for ionizing gas and collecting such ions.

17. The method of claim 16 wherein said pumping is performed by a sputter-ion pump, and a single power supply is used for said sputter-ion pump and said sensing unit.

18. The method of claim 15 wherein said pumping is performed by an anode cell type of sputter-ion pump, said sensing unit is an anode cell type of pressure sensing unit, and wherein said sensing unit has more anode cells than said sputter-ion pump and performs little or no pumping relative to the pumping of said sputter-ion pump.

19. The method of claim 15 wherein the pumping speed with which said sensing unit is evacuated is approximately equal to the value of said conductance.

* * * * *

UNITED STATES PATENT AND TRADEMARK OFFICE
CERTIFICATE OF CORRECTION

PATENT NO. : 4,047,102

DATED : September 6, 1977

INVENTOR(S) : Kimo M. Welch

It is certified that error appears in the above—identified patent and that said Letters Patent is hereby corrected as shown below:

```
Col. 3, line 50, change "has" to --had--;
Col. 4, line 14, insert --on-- before "other";
Col. 4, line 50, change "soidum" to --sodium--;
Col. 5, line 26, change "installation" to --installations--;
Col. 5, line 50, change " consistancy" to --constancy--;
Col. 5, line 58, change "cathod" to --cathode--;
Col. 6, line 48, change "10" to --40--;
Col. 7, line 59, change "a" (second occurrence) to --n--;
Col. 8, lines 47-48, change "amplication" to --amplification--;
Col. 8, line 59, change "(mSu/C + 1" to
```

$$-- \frac{mS_u}{C} + \frac{m}{n} + 1 --$$

```
Col. 8, line 60, change "m = 1 >>n" to --m = 1 <<n--;
Col. 8 lines 65 and 66 change "amplication" to --amplification--
Col. 8, line 68, change "chamber" to --chambers--;
Col. 9, line 21, change "Thereforem" to --Therefore,--;
Col. 9, lines 21-22, change "amplication" to --amplification--.
```

Signed and Sealed this

Seventh Day of July 1981

[SEAL]

Attest:

RENE D. TEGTMEYER

Attesting Officer  Acting Commissioner of Patents and Trademarks